United States Patent [19]
Kobayashi et al.

[11] Patent Number: 5,576,183
[45] Date of Patent: Nov. 19, 1996

[54] MONOCLONAL ANTIBODY RECOGNIZING FK506-BINDING PROTEIN, METHOD FOR ASSAYING FK506-BINDING PROTEIN LEVEL, AND KIT THEREFOR

[75] Inventors: Masakazu Kobayashi, Takarazuka; Kazuyuki Ohtsuka, Osaka; Hirokazu Tanaka, Takarazuka; Mineo Niwa, Muko, all of Japan

[73] Assignee: Fujisawa Pharmaceutical Co., Ltd., Osaka, Japan

[21] Appl. No.: 379,563
[22] PCT Filed: Aug. 11, 1993
[86] PCT No.: PCT/JP93/01136
 § 371 Date: Feb. 10, 1995
 § 102(e) Date: Feb. 10, 1995
[87] PCT Pub. No.: WO94/04700
 PCT Pub. Date: Mar. 3, 1994

[30] Foreign Application Priority Data

Aug. 12, 1992 [JP] Japan ..................... 4-214967

[51] Int. Cl.$^6$ .................... G01N 33/53; C07K 16/18
[52] U.S. Cl. ............... 435/721; 530/388.27; 530/388.25
[58] Field of Search .............. 530/388.22, 388.25; 435/7.21, 240.27, 70.21, 172.20, 800; 436/548

[56] References Cited

U.S. PATENT DOCUMENTS 4,894,366 1/1990 Okuhara et al.

FOREIGN PATENT DOCUMENTS

WO-A-9307269 4/1993 WIPO.

OTHER PUBLICATIONS

Nature, vol. 357, Jun. 25, 1992, Stephen J. O'Keefe, et al., "FK–506– And CsA–Sensitive Activation Of The Interleukin–2 Promoter By Calcineurin", pp. 692–694.

Nature, vol. 357, Jun. 25, 1992, Neil A. Clipstone, et al., "Identification Of Calcineurin As A Key Signalling Enzyme In T–Lymphocyte Activation", pp. 695–697.

Nature, vol. 341, Oct. 26, 1989, John J. Siekierka, et al., "A Cytosolic Binding Protein For The Immunosuppressant FK506 Has Peptidyl–Prolyl Isomerase Activity But Is Distinct From Cyclophilin", pp. 755–757.

Nature, vol. 341, Oct. 26, 1989, Matthew W. Harding, et al., "A Receptor For The Immunosuppressant FK506 Is A Cis–Trans Peptidyl–Prolyl Isomerase", pp. 758–760.

J. Am. Chem. Soc., 1991, vol.113, pp. 1409–1411, Heinz Fretz, et al., "Rapamycin And FK506 Binding Proteins (Immunophilins)".

Proc. Natl. Acad. Sci, USA, vol. 88, Jul. 1991, pp. 6229–6233, Thomas Hultsch, et al., "Immunophilin Ligands Demonstrate Common Features Of Signal Transduction Leading To Exocytosis Or Transcription".

Transplantation Proceedings, vol. 23, No. 6, Dec. 1991, pp. 2760–2762, J. E. Kay, et al., "Uptake Of FK 506 By Lymphocytes And Erythrocytes".

Nature, vol. 256, Aug. 7, 1975, G. Köhler, et al., "Continuous Cultures Of Fused Cells Secreting Antibody Of Predefined Specificity", pp. 495–497.

Seuier et al. Clin Chem 27:1797–1806, 1981.

Jayaraman et al. Journal Biol. Chem. 267:9474–7 1992.

Rosborough et al. Transpl. Proc. vol. 23:2890–93, 1991.

Tsudo et al. PNAS USA 83:9694–8 1986.

Tamuro et al. Transpl. Proc. 19:23–9, 1987.

Callebaut et al, *Proc. Natl. Acad. Sci. USA*, vol. 89, pp. 6270–6274 (1992).

Lebeau et al, *The Journal of Biological Chemistry*, vol. 267, pp. 4281–4284 (1992).

Murthy et al, *Clin. Chem.*, vol. 38, pp. 1307–1310 (1992).

Kobayashi et al, *Transplantation Proceedings*, vol. 25, pp. 655–657 (1993).

Primary Examiner—Paula K. Hutzell
Attorney, Agent, or Firm—Oblon, Spivak, McClelland, Maier & Neustadt, P.C.

[57] ABSTRACT

The present invention relates to a monoclonal antibody (anti-FKBP antibody) which recognizes an antigenic determinant in an FK506-binding protein and does not inhibit the binding between an FK506-binding protein and FK506, a method for assaying an FKBP level in plasma, comprising reacting an immobilized anti-FKBP antibody, an enzyme-labelled FK506 and FKBP in a specimen, and assaying the degree of color development of an enzyme substrate, and a kit for the assay. According to the present invention, the FKBP level in plasma which affects the immunosuppressive action of FK506 can be assayed more precisely with ease, which in turn enables setting the optimal dose of FK506 in close accordance with the condition of individual patients.

3 Claims, No Drawings

MONOCLONAL ANTIBODY RECOGNIZING FK506-BINDING PROTEIN, METHOD FOR ASSAYING FK506-BINDING PROTEIN LEVEL, AND KIT THEREFOR

TECHNICAL FIELD

The present invention relates to a monoclonal antibody recognizing a protein which binds with FK506 (FK506-binding protein) having an immunosuppressive activity, a method for assaying the level of an FK506-binding protein and a kit therefor, which are usable in the medical field.

BACKGROUND ART

A compound designated as FK506 or FR-900506 is well known to have a potent immunosuppressive activity and is usable as an agent for the prophylaxis and treatment of rejection by organ transplantation and autoimmune diseases (for example, Japanese Patent Unexamined Publication No. 14818/1986).

However, the activity is so potent that the determination of the optimal dose is of utmost importance and administration of an amount capable of inducing effective immunosuppressive activity without side effects is extremely important.

Later studies revealed that the immunosuppressive action of FK506 is caused by the binding with an intracellular FK506-binding protein (hereinafter indicated as FKBP) having similar activity to peptidylprolyl cis-trans isomerase [for example, Nature, 357, 692–694 and 695–697 (1992)].

FKBP is known to include several types depending on the molecular weight, such as FKBP-12 (molecular weight 12 KDa), FKBP-13 (molecular weight 13 KDa), FKBP-25 (molecular weight 25 KDa), FKBP-56 (molecular weight 56 KDa), FKBP-80 (molecular weight 80 KDa) and the like, and their structures have been already identified.

See, for example, Nature, 341, 755–757 and 758–760 (1989), J. Am. Chem. Soc. 113, 1409–1411 (1991), Proc. Natl. Acad. Sci., 88, 6229–6233 (1991) and the like.

Also, the production of an FKBP having a molecular weight of 11,819 daltons and 107 amino acids by genetic engineering has been already reported [Nature, 346, 671–674 (1990)].

It has also been reported that FK506 most strongly binds with FKBP-12 from among those FKBPs and its affinity constant (Kd) is 0.4 nM, and that FKBP-12 is present in large amounts not only in lymphocytes but also in various tissues inclusive of erythrocytes [Trans. Proc. 23 (6), 2760–2762 (1991)].

In view of the fact that, when FKBP-12 is given to mouse MLR system together with a certain amount of FK506, the immunosuppressive effect of FK506 is inhibited in proportion to the amount of the FKBP-12 added, FK-506 will be bound with FKBP-12 in plasma if it is present in blood, and the immunosuppressive effect cannot be obtained to the degree expected from the concentration of FK506 in plasma. Considering that erythrocytes of patients who underwent operation lyse and FKBP-12 in erythrocytes circulates through plasma, and that patients show different sensitivities, there has been a demand for the development of a technique which enables precise assay of FKBP level in plasma, whereby patient's sensitivity to FK506 is presumed and more desirable FK506 level in plasma can be determined.

DISCLOSURE OF THE INVENTION

It is therefore an object of the present invention to provide a monoclonal antibody recognizing FKBP, a method for precisely assaying the level of FKBP in plasma for the determination of desirable FK506 level in plasma, and a kit to be used for the assay.

The present inventors have conducted intensive studies and succeeded in producing a monoclonal antibody which recognizes an antigenic determinant in FKBP and does not inhibit the binding between FKBP and FK506, and established a method for precisely assaying the level of FKBP in plasma and a kit for the assay.

Accordingly, the present invention relates to a monoclonal antibody which recognizes an antigenic determinant in FKBP and does not inhibit the binding between FKBP and FK506, a method for assaying an FKBP level, comprising reacting an immobilized monoclonal antibody with an enzyme-labelled FK506 and FKBP in a specimen, a method for assaying an FKBP level, comprising reacting an immobilized FKBP with an enzyme-labelled FK506 and FKBP in a specimen, and a kit for FKBP level assay, comprising said monoclonal antibody, FKBP and an enzyme-labelled FK506.

The monoclonal antibody which recognizes an antigenic determinant in FKBP and does not inhibit the binding between FKBP and FK506 (said monoclonal antibody is hereinafter indicated as anti-FKBP antibody), can be produced by, for example, the conventional cell fusion method, such as the basic method of Kohler and Milstein [Nature, 256, 495 (1975)].

Preferably, spleen cells obtained from mice immunized with FKBP and mouse myeloma cells are fused to give a hybridoma, from which a monoclonal antibody, which recognizes an antigenic determinant in FKBP and does not inhibit the binding between FKBP and FK506, can be produced by the method as exemplified by Example 1 or Example 2 to be mentioned below. More preferably, the antibody is of IgG or IgM class and most preferably a subclass such as $IgG_{1\lambda}$ or $IgG_{1\kappa}$. The method of the present invention particularly affords an anti-FKBP antibody which reacts with 12 kd FKBP alone or with both 12 kd and 30–35 kd FKBPs.

The method for assaying an FKBP level of the present invention is generally classified into a two-step method wherein an anti-FKBP antibody is used to selectively assay the desired FKBP alone, and a one-step method wherein all FKBP capable of binding with FK506 is nonselectively assayed.

The two-step method includes 1) immobilizing an anti-FKBP antibody, which recognizes an antigenic determinant in an FKBP of the objective kind and does not affect the binding between FKBP and FK506, on a solid phase such as an immunoplate by the use of IgG such as anti-mouse IgG (H+L); 2) reacting the immobilized anti-FKBP antibody with a specimen containing FKBP (or serially diluted FKBP when calibration curve is drawn), and an FK506 labelled with an enzyme such as peroxidase (hereinafter indicated as POD) which is, for example, exemplified by FK506-C32(LA)-POD produced in the manner as in Example 1 to be mentioned below; and 3) lastly assaying an FKBP level by measuring absorbance to determine, by the use of an enzyme substrate solution such as an o-phenylene diamine and hydrogen peroxide solution, color development of the substrate, which is in proportion to the amount of the enzyme-labelled FK506 trapped by the FKBP bound with the anti-FKBP antibody.

The one-step method includes 1) immobilizing an FKBP such as FKBP-12 on a solid phase such as an immunoplate; 2) reacting the immobilized FKBP with an enzyme-labelled FK506 such as FK506-C32(LA)-POD together with a specimen containing FKBP (or serially diluted FKBP when calibration curve is drawn); and 3) after the competitive reaction of the FKBP in the specimen and the immobilized FKBP, determining, by the use of an enzyme substrate solution as used in the two-step method, a decrease of the enzyme-labelled FK506 trapped by the immobilized FKBP, which reflects the amount of FKBP in the specimen. The FKBP level in the specimen is assayed thereby.

The one-step method is characterized in that the total FKBP level in the specimen, which affects the activity of FK506, can be assayed, since the enzyme-labelled FK506 reacts with every FKBP in the specimen.

The anti-FKBP antibody of the present invention can be used for the assay by the aforementioned two-step method as an FKBP level assay kit, in combination with an FKBP standard product and an enzyme-labelled FK506.

The present invention enables easy and more precise assay of the level of FKBP in plasma, which exerts influences on the immunosuppressive effect of FK506, as well as provision of important data for the determination of the optimal dose of FK506.

In addition, the dose of FK506 can be determined in close accordance with the condition of individual patients in actual clinical situations, since both the selective assay of the level of a specific FKBP (e.g. FKBP-12) alone and the assay of the total FKBP level as occasion demands have been made possible.

The present invention is explained in more detail by illustrative examples, to which the invention is not limited.

EXAMPLE 1

Production of anti-FKBP antibody (1) Production and characteristics of FKBP-12

A DNA (48 mer) corresponding to the C-terminal of FKBP-12 was synthesized using a DNA synthesizer (manufactured by Applied Biosystem) from the DNA sequence reported by S. L. Schreiber et al. of Harvard University [Nature, 346, 671–674 (1990)].

5'-CCACATGCCACTCTCGTCTTCGATGTG-
GAGCTTCTAAAACTGGAATGA-3' (SEQ ID NO: 1)

The terminal of said 48-mer was labelled with $^{25}P$ and by using same as a probe, human T-cell cDNA library HL1016b (CLONTECH), 500,000 plaques, was screened, whereby one positive plaque was obtained. A fragment [pUC-23(Ec)] containing FKBP-12 cDNA was subcloned from this plaque. The pUC-23(Ec) was subjected to sequencing to find deletion of 1–32 DNA sequence corresponding to the N-terminal. DNA for complementation of the deficient portion and about 80 b.p. AT rich silent mutant N-terminal DNA synthesized for enhancing the expression in Escherichia coli were incorporated as an EcoRI-BamHI site into a plasmid capable of expressing under the control of a tryptophan promotor, whereby an expression vector pFKBP333 was obtained. Using this vector, E. coli HB101 was transformed to give an expression cell HB101/pFKBP(AT)311. The cell was incubated in L-amp. broth for 19 hours and protein synthesis was induced by the addition of IAA (Indol-Acrylic acid) to the final concentration of 90 μg/ml. E. coli was harvested, and the cells were disrupted with a French Press in 50 mM Tris-HCl, 2 mM β-ME, 2 mM $CaCl_2$, 10 mM $MgCl_2$ and 5% glycerol and centrifuged at 4° C. for 30 minutes at 6,000×g. The supernatant was heat-treated at 60° C. for 15 minutes, centrifuged (4° C., 6,000×g, 45 min+4° C., 18,000×g, 20 min×2), dialyzed [20 mM Tris-HCl (pH 7.4), 4° C., overnight], and subjected to DEAE-Toyo Pearl 650M-reversed phase HPLC (C4) to purify FKBP-12.

(2) Immunization of mice with FKBP-12

FKBP-12 in phosphate buffer (hereinafter indicated as PBS), 250 μg/ml, 0.1 ml, and the equivalent amount of Freund's Complete Adjuvant (FCA) were mixed and used for intraperitoneal immunization of BALB/c mice. The same amount of FKBP-12 was mixed with Freund's Incomplete Adjuvant (FIA) and used for several times of intraperitoneal immunization every ca. 10 days. (3) Assay of antibody titer in blood Blood (10 μl) was taken from the tail vein of mice, mixed with PBS (990 μl) and used as a specimen. For assay, an FKBP-12 PBS solution (10μg/ml, 50 μl) was placed in immunoplate wells and reacted at room temperature for 3 hours to allow binding on the surface. Then, the wells were washed and the binding site was blocked with 0.2% milk blocker-PBS. After washing again, the diluted serum specimen as obtained above was added and reacted at room temperature for 1 hour. Then, anti-mouse IgG (H+L)-POD (100 μl/well, manufactured by Vector Lab.) was added and reacted at room temperature for 1 hour. After washing, color was developed by a conventional method using o-phenylene diamine.

(4) Production of anti-FKBP-12 antibody

The mice which showed increases in antibody titer were given an injection of FKBP-12 [250 μg/ml (PBS), 0.2 ml] from the tail vein for final immunization. Four days later, the spleen was removed to prepare $1.44 \times 10^8$ spleen cells. Alongside therewith, mice myeloma cells P3X63Ag8U.1 were adjusted to a concentration of $2.9 \times 10^7$ cells and subjected to cell fusion in 50% PEG 4000 (final concentration). Then, fused cells were screened in HAT medium in a 24 well plate at $10^6$ cells/m1×1 ml/well. Two weeks later, 144 wells, in which cells grew in HAT medium, were screened for anti-FKBP-12 antibody production. Specifically, in the assay of antibody titer in blood, FKBP-12 (5 μg/ml, final) was also added when a specimen containing anti-FKBP-12 antibody was added for reaction, and the wells which failed to develop color in the presence of FKBP-12 were selected. Furthermore, 32 clones having high antibody titers against FKBP-12 were selected.

(5) Selection of anti-FKBP-12 antibody which recognizes FKBP-12 and does not inhibit the binding between FK506 or FK506-C32(LA)POD and FKBP-12

An anti-mouse IgG(H+L) was bound with a solid phase and the screened antibody was bound. Then, FKBP-12 (50 μl, 1μg/ml) and FK506-C32(LA)-POD obtained in the following (6) (diluted 1000-fold, 50 μl) were added to allow coexistence, and the clones which showed increase in absorbance at 490 nm due to the reaction with o-phenylene diamine were selected. Disappearance of the color development in the presence of FK506 (10 μg/ml) suggests recognition of FK506 of FK506-C32(LA)-POD by FKBP-12 bound with the anti-mouse IgG(H+L). As a result, five kinds of antibodies (5-1-A5,5 -1-B3, 5-1-C 5, 5-2-D1 ($IgG_1$), 5-4-D2) were obtained by the immunization method using FKBP-12 as an antigen; and the total of seven kinds of monoclonal antibodies were obtained by the immunization method using urea-denatured FKBP-12 as an antigen as in the following (7)-IA4 (IgM), 3A8 ($IgG_3$), IF7, 3B8 - and by the immunization method using FKBP-12 bound with ovalbumin as an antigen as in the following (8)-4F 8.

(6) Production of FKBP506-C32(LA)-POD

Succinic acid-FR-90056 substance half ester (230 mg) obtained in the same manner in Example 1 of Japanese Patent Unexamined Publication No. 92659/1989, N-hydroxysuccinimide (35 mg) and a solution (10 ml) of 1-ethyl-3-(3-dimaethylamino-propyl) carbodiimide hydrochloride (43 mg) in methylene chloride were stirred at room temperature for 5 hours. The reaction mixture was washed with water and dried. The solvent was distilled away and the obtained residue (250 mg) was stirred with 11-aminoundecanoic acid (120 mg) and triethylamine (60 mg) in a solvent of dimethylformamide-water (1:1, 20 ml) at room temperature for 6 hours. The reaction mixture was washed with water and dried, and the solvent was distilled away. The obtained residue was applied to a silica gel column, using chloroform as a developing solvent, to give 120 mg of 17-allyl-1,14-dihydroxy-12-[2-(4-N-(10-carboxydecyl)-(4-amino-1,4-dioxo-1-butyloxy))-3-methoxycyclohexyl)-1-methylvinyl]-23, 25-dimethoxy-13,19,21,27-tetramethyl-11, 28-dioxa-4-azatricyclo[22.3.1.0$^{4,9}$]octacos-18-ene-2,3,10,16-tetraone.

NMR (CDCl$_3$, δ): 1.2–1.4 (m), 5.9–6.1 (1H, m) FAB MASS : 1109 (M+Na)$^+$

Using the above-mentioned compound, an FK506-C32(LA)-POD solution was obtained in the same manner as in Example 1, 3) of Japanese Patent Unexamined Publication No. 92659/1989 by reacting horseradish peroxidase.

(7) Preparation of urea-denatured FKBP-12

Urea (312 mg) was added to a 0.08% aqueous trifluoroacetic acid solution (460 μl) containing FKBP-12 (847 μg/ml) and the mixture was stirred at room temperature to prepare 650 μl of a solution of FKBP-12 (600 μg/ml), which was used for immunization.

(8) Preparation of ovalbumin-binding FKBP-12

FKBP-12 (1032 μg, used was 1032 μl of 1 mg/ml) and a solution (1032 μl) of ovalbumin (Sigma, Lot No. 76F-8040) in PBS (2 mg/ml) were mixed. Thereto was dropwise added 0.62 ml of a 0.13M glutaraldehyde-PBS solution. The mixture was stirred at room temperature for 14 hours and dialyzed 3 times against PBS (1 l) and used as an immunogen.

The mixing ratio of FKBP-12 and ovalbumin was FKBP-12 1032 μg : ovalbumin 2064 μg, and the solution amount was 2.7 ml.

EXAMPLE 2

Production of anti-FKBP-12 antibody (1) Mice were immunized in the same manner as in Example 1, (1) and (2).

(2) Determination of antibody titer in blood

A solution (50 μl) of FKBP-12 (20 μg/ml) in PBS was dispensed to each well of a 96 well plate for ELISA and left standing at 4° C. overnight. The FKBP-12 solution in the wells was removed by suction and the wells were washed 3 times with a 0.05% Tween 20/PBS solution. A 0.2% milk/PBS solution (250 μl) was added to each well of the plate and the plate was left standing at room temperature for 30 minutes. The 0.2% milk/PBS solution in the wells was removed by suction, a solution (100 μl) of each anti-serum diluted with a 0.2% milk/0.05% Tween 20/PBS solution was added to the wells, and the wells were left standing at room temperature for 2 hours. Then, the dilute anti-serum in the wells was removed by suction and the wells were washed 3 times with a 0.05% Tween 20/PBS solution. An alkaline phosphatase-labelled anti-mouse IgG(H+L) solution diluted 1,000-fold with a 0.2% milk/0.05% Tween 20/PBS solution was added to each well by 100 μl and the wells were left standing at room temperature for 2 hours. The alkaline phosphatase-labelled anti-mouse IgG(H+L) solution in the wells was removed by suction and the wells were washed 5 times with a 0.05% Tween 20/PBS solution. Then, a solution of 0.1 mM 4-methylumbelliferyl phosphate (4MU-P, Sigma) in a buffer (10 mM diethanolamine/0.5% MgCl$_2$/H$_2$O) was added to each well by 100 μl and the wells were left standing at room temperature for 15 minutes. The fluorescence intensity (excitation; 360 nm, emission; 460 nm) of each well was read on a fluorescence plate reader.

(3) The mouse having the highest antibody titer was selected and given an injection of 0.2 ml of a PBS solution containing 1.5 mg/ml of FKBP-12 from the tail vein for final immunization at 10 days after the fourth injection.

(4) Cell fusion

Cells were fused by the same method as in Example 1–(4) to give hybridomas (3-3-D4-C6, 2C1-87, 3F4-70).

(5) Production and purification of antibody

The hybridomas 2C1-87 and 3F4-70 obtained by screening and cloning were respectively inoculated in an F75 flask at 5×10$^4$ cells/ml (50 ml/F75) and cultured for 4 days. The culture was centrifuged, washed twice with a medium without serum, and suspended in 0.5 ml. A hybridoma suspension (0.5 ml) was intraperitoneally transplanted into BALB/C mice (BALB/C, female, 6 weeks of age) that received intraperitoneal injection of pristane (0.5 ml) two weeks earlier. Ten days later, the mice underwent a laparotomy and ascites (5 ml) was obtained from each mouse. The respective ascites was purified using Affigel protein A MAPS-II kit (Bio-Rad) to give purified anti-FKBP-12 monoclonal antibodies 2C1-87 (subtype: IgG$_{1\lambda}$) and 3F4-70 (subtype: IgG$_{1\kappa}$). The hybridoma 3-3-D4-C6 was cultured in the same manner and anti-FKBP-12 monoclonal antibody 3-3-D4-C6 (subtype: IgM) was obtained.

EXAMPLE 3

Assay of FKBP-12 level (two-step method)

A solution of anti-mouse IgG(H+L) (10 μg/ml) is placed in an immunoplate by 50 μl per well, left standing at 4° C. overnight, and washed 3 times with 0.05% Tween 20-PBS. 0.2% Milk blocker-PBS (200 μl/well) is allowed to react at room temperature for 1 hour for blocking the binding site, and 0.2% milk blocker-0.05% Tween 20-PBS (50 μl/well) and the anti-FKBP-12 antibody (5-2-D1) culture (50 μl/well) obtained in Example 1 are added and the wells are left standing at 4° C. overnight. The wells are washed 3 times with 0.05% Tween 20-PBS and reacted with FKBP-12 (50 μl/well) serially diluted with 0.05% Tween 20-PBS, at room temperature for 2.5 hours. The wells are washed 3 times with 0.05% Tween 20-PBS. An FK506-C32(LA)-POD solution (50 μl/well) diluted 500-fold with PBS is added and the wells are left standing at room temperature for 2 hours. The wells are washed 5 times with 0.05% Tween 20-PBS and subjected to color development by a conventional method using an o-diphenylamine/hydrogen peroxide solution. The degree of color development, which is subject to change according to the amount of FKBP-12, is assayed.

Normal human plasma was assayed instead of the serially diluted FKBP-12 by the above-mentioned method. The FKBP-12 level was about 100 ng/ml.

The result was confirmed to be accurate from a reagent showing the recovery ratio of FKBP-12 (1 μg) added to normal human plasma (1 ml).

EXAMPLE 4

Assay of FKBP level (one-step method)

A solution of FKBP-12 (20 μg/ml) is placed in an immunoplate by 50 μl per well and left standing at 4° C. overnight. The wells are washed 3 times with 0.05% Tween 20-PBS. Thereto is added 1% gelatin-PBS (200 μl) and the wells are left standing at room temperature for 1 hour and washed once with 0.05% Tween 20-PBS. Then, a solution (50 μl) of FKBP-12 serially diluted with 0.05% Tween 20-PBS and a solution (50 μl) of FK506-C32(LA)-POD diluted 1,000-fold with PBS are added and reacted at room temperature for 4 hours. The wells are washed 5 times with 0.05% Tween 20-PBS and subjected to color development using an o-phenylene diamine/hydrogen peroxide solution as in conventional ELISA.

protein and FK506, and wherein said FK506-binding protein is human FKBP-12.

2. A method for assaying an FK506-binding protein level in a sample, comprising:
   (i) reacting an immobilized monoclonal antibody of claim 1 with an enzyme-labelled FK506 and a sample which may contain an FK506-binding protein, for a time sufficient to form an enzyme-labelled FK506-FK506-binding protein-immobilized monoclonal antibody complex; and
   (ii) measuring the amount of said enzyme-labelled FK506-FK506-binding protein-immobilized monoclonal antibody complex formed
   wherein said FK506-binding protein is human FKBP-12.

---

---

What is claimed is:

1. A monoclonal antibody which recognizes an antigenic determinant in an FK506-binding protein, wherein said monoclonal antibody binds both to said FK506-binding protein and to said FK506-binding protein bound to FK506 without inhibiting the binding between said FK506-binding 3. A kit for assaying an FK506-binding protein level, comprising the monoclonal antibody of claim 1, an FK506-binding protein and an enzyme-labelled FK506, wherein said FK506-binding protein is human FKBP-12.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="PRIMER"

( x i ) SEQUENCE DESCRIPTION: SEQ ID NO:1:

CCACATGCCA CTCTCGTCTT CGATGTGGAG CTTCTAAAAC TGGAATGA    48